United States Patent [19]

Deyoe et al.

[11] 3,954,809

[45] May 4, 1976

[54] PREPARATION OF L-ASCORBATE 2-SULFATE FROM L-ASCORBIC ACID

[75] Inventors: Charles W. Deyoe; Paul A. Seib; R. Carl Hoseney, all of Manhattan, Kans.

[73] Assignee: Kansas State University Research Foundation, Manhattan, Kans.

[22] Filed: Jan. 22, 1973

[21] Appl. No.: 325,652

[52] U.S. Cl. .................................... 260/343.7
[51] Int. Cl.² .................................. C07D 307/62
[58] Field of Search ........................ 260/343.7

[56] References Cited
OTHER PUBLICATIONS

Allaudeen et al., Arch. Biochem. Biophys. 140:245 (1970).
Tolbert et al., Federation of American Societies for Experimental Biology, 30, 1819 (Mar. 1971).
Mumma et al., Isolation of Ascorbic Acid 2–Sulfate From Selected Pat. Organs., Biochimica et Biophysica Acta, pp. 249–253, 7-19-72.

*Primary Examiner*—Raymond V. Rush
*Attorney, Agent, or Firm*—Schmidt, Johnson, Hovey & Williams

[57] ABSTRACT

A method is provided for the synthesis of L-ascorbate 2-sulfate compounds and salts thereof which comprises reacting L-ascorbic acid or the salts thereof of the formula

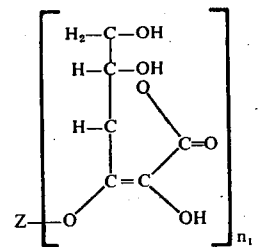

where Z represents hydrogen or a cation capable of bonding with L-ascorbic acid, and $n_1$ is the valence of Z, with a base-sulfur trioxide complex of the formula

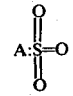

where A represents a tertiary amine, tertiary amide, ether or thioether, the reaction being carried out in a compatible solvent and in the presence of sufficient base to render the $C_2$ hydroxyl of the L-ascorbic acid more ionized than the $C_5$ and $C_6$ hydroxyls thereof. The process effects quantitative conversion of L-ascorbic acid to L-ascorbate 2-sulfate, and pure compounds of the latter are isolated in good yields. Such compounds have been found to act as stable vitamin C sources in food systems or the like.

9 Claims, No Drawings

PREPARATION OF L-ASCORBATE 2-SULFATE FROM L-ASCORBIC ACID

BACKGROUND OF THE INVENTION

This invention is concerned with providing an improved, more economical method for the production of L-ascorbate 2-sulfate compounds and their associated salts; more particularly, it is directed to such a method which produces these compounds by using L-ascorbic acid or its salts as the starting material, rather than a more expensive derivative of this acid.

In our co-pending patent application entitled "PREPARATION AND USE OF L-ASCORBATE 2-SULFATE COMPOUNDS", Ser. No. 325,650, filed Jan. 22, 1973 and now abandoned, a method was disclosed for the production of L-ascorbate 2-sulfate compounds wherein selected 5,6-acetal derivatives of L-ascorbic acid and their salts were employed as the starting material. The sulfation of these compounds was effected by reacting the acetal derivatives with a base sulfur-trioxide complex in a compatible solvent while maintaining the acid concentration of the reaction medium at a sufficiently low level to prevent inhibition of the desired reaction. This method using apolar solvents produced the desired L-ascorbate 2-sulfate compounds and their associated salts in yields of about 75%, and quantitative yields were obtained by using protic solvents. In either solvent system, the final compounds were essentially 100% pure. These results were shown to be superior to any of the methods previously reported in the prior art.

Although that method proved to be extremely efficient in practice, alternate processes have been sought for several reasons. Most importantly, that method as disclosed requires that certain defined 5,6-acetal derivatives of L-ascorbic acid or the salts thereof, be employed as the starting material of the sulfation reaction. As can be appreciated, in some situations it is desirable to employ simple L-ascorbic acid or its salts without any acetal groups in order to produce the desired compounds. This can occur when the formation or removal of the blocking group serves to increase the cost or complexity of the process.

Therefore, there is a need in the art for a method which produces L-ascorbate 2-sulfate compounds and salts thereof by utilizing L-ascorbic acid or its salts as the starting material of the sulfation reaction. This could serve to lower the costs of producing the valuable end products, as well as simplifying the overall chemistry of the reaction sequence. The latter factor is important when it is desired to use the products of the reaction as additives in food products, because a lesser number of reaction steps generally facilitates purification of the end product.

As further disclosed in our co-pending patent application, certain defined L-ascorbate 2-sulfate salts have been found to be extremely stable sources of vitamin C in food systems. Hence, such salts find utility in the chemical and food processing industries as vitamin additives. Typical examples of these uses involve adding the salts to fruit and vegetable juices, jams, jellies, preserves, pastries, bread and dairy products.

It is, therefore, a primary object of the present invention to provide a method for producing L-ascorbate compounds and their associated salts wherein L-ascorbic acid or its salts are employed as the starting material.

It is another important object to provide such method wherein a lesser number of steps are required in the reaction sequence in order to produce the desired compounds.

SUMMARY

In accordance with the foregoing objects, an improved method for the production of L-ascorbate 2-sulfate compounds and their related salts broadly comprises reacting L-ascorbic acid or its salts with a base-sulfur trioxide complex in the presence of sufficient free base to render the $C_2$ hydroxyl of the acid more ionized than the $C_5$ and $C_6$ hydroxyls thereof. More specifically, L-ascorbic acid and salts thereof which correspond to the formula

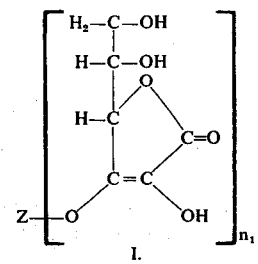

I.

where Z represents hydrogen or a cation capable of bonding with the L-ascorbic acid, and $n_1$ represents the valence of Z is reacted with a base-sulfur trioxide complex of the formula

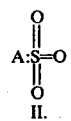

II.

where A represents a tertiary amine, tertiary amide, ether or thioether. In the initial sulfation reaction, all of the defined bases are operable within the complex, but preferably such tertiary amines as pyridine, trimethylamine, triethylamine, tributylamine, N,N-dimethylaniline, N-methylmorpholine, N,N-dimethylbenzylamine, isomeric lutidines, isomeric picolines or quinoline are used for this purpose. Typical members of the other defined classes of bases are N,N-dimethylformamide, N-methylacetanilide, N,N-dimethylbenzamide, dioxane, tetrahydrofurane, bis(2-chloroethyl) ether and diethylsulfide. The preferred cations in the defined salts include the alkali and alkaline earth metals and tertiary amine cations such as sodium, potassium, magnesium, calcium and trimethylamine cations.

As will be discussed hereinafter, it is sometimes advantageous to select a solvent medium of particular chemical characteristics when certain amine-sulfur trioxide complexes are employed. For example, if pyridine sulfur-trioxide complex is used, best results are obtained when a dipolar aprotic solvent such as N,N-dimethylformamide is employed. Conversely, when the preferred amines such as trimethylamine are used as the amine portion of the complex, protic solvents such as water can be utilized without difficulty.

The most important factor in the present invention which allows the use of L-ascorbic acid or its salts as the starting material for the sulfation reaction is the presence of sufficient base during this reaction to render the $C_2$ hydroxyl of the acid more ionized than the $C_5$ and $C_6$ hydroxyls thereof. In accordance with conventional chemical naming procedures, the following formula will show the correct numbering scheme of the carbon atoms throughout the ring and side chain.

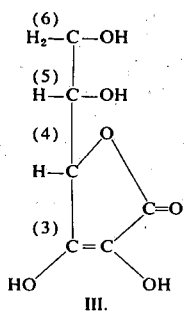

III.

As can be seen, sulfation at the 5 and/or 6 hydroxyls is an undesirable side reaction because it lowers the ultimate yields of the 2-sulfated products. Further, such mixtures of products are undesirable in that they are oftentimes difficult to separate, thereby making purification of the 2-sulfate product more complicated.

In accordance with the invention, it has been discovered that if sufficient free base is present during the sulfation reaction, the $C_2$ hydroxyl will become more ionized and therefore more reactive than the $C_5$ and $C_6$ hydroxyls. This increased ionization will cause the $C_2$ hydroxyl to be selectively sulfated, with little or none of the undesirable side reactions occurring. For the general case, the amount of base required can be defined as that amount needed to render the $C_2$ hydroxyl more ionized than the $C_5$ and $C_6$ hydroxyls thereof. If, as in the preferred embodiment, water is employed as the solvent medium, this amount of base can be translated into hydronium ion concentration terms. In such a case, a basic pH is required, with a range of from 8 to 13.5 being preferred. In still further preferred embodiments, a pH of from 10 to 10.5 has advantageously been maintained.

In other embodiments, it has sometimes been found helpful to conduct the sulfation reaction at elevated temperatures, for example at from 40° to 90° C. This serves to increase the solubility of the amine-sulfur trioxide complex as well as to increase the reaction rate. In many cases, the reaction is very slow at room temperatures, although it will eventually occur; however, upon heating, the reaction rate is significantly increased, thereby making the entire process more feasible for commercial scale production.

DETAILED DESCRIPTION

As explained above, the key step of the synthesis of the compounds of this invention involves reacting L-ascorbic acid or its salts with a base-sulfur trioxide complex in the presence of sufficient free base to enhance the sulfation of the $C_2$ hydroxyl and opposed to that of the $C_5$ and the $C_6$ hydroxyls.

The base-sulfur trioxide complexes to be utilized in this invention are broadly represented by formula II. While all of the defined bases can be employed in this context, it is preferred that the tertiary amines specified above be used as the base portion of the complex. In the reaction, this complex is generally added in greater than equimolar amounts with respect to the acid in order to increase the ultimate reaction rate; however, substantially equimolar amounts can be added without impairing the overall reaction. The complexes can be introduced directly into the reaction mixture in all cases or they can be produced in situ by conventional techniques at lowered temperatures if an aprotic solvent medium is employed.

In order to achieve optimum results with the present method, it is sometimes advantageous to select the characteristics of the solvent medium with respect to the particular base-sulfur trioxide complex chosen. One requirement of the solvent is that it be capable of dissolving a substantial portion of the reactants. Additionally, a solvent medium should be selected that will not hinder the desired sulfation reaction. For example, if pyridine sulfur-trioxide is employed, a dipolar aprotic solvent medium is advantageously used, due to the low base strength of the pyridine. Typical examples of dipolar aprotic solvents, i.e. those which do not readily ionize to give off free protons in aqueous systems, include N,N-dimethylacetamide, acetone, nitromethane, acetonitrile, nitrobenzene, benzonitrile, hexamethylphosphoramide, and N-methyl-2-pyrrolidone. With amines such as pyridine, the tertiary amides, ethers or thioethers which have ionization constants of $10^{-6}$ and below (in aqueous solutions at room temperatures), solvents of protic character such as water tend to interfere with the overall reaction, by converting the sulfur trioxide of the complex to sulfuric acid.

In a preferred embodiment of the present invention, tertiary amines having relatively higher ionization constants are employed as the base portion of the complexes, for example, those having ionization constants of above about $10^{-6}$. In such cases, protic solvents such as water or water-alcohol mixtures can be utilized with good results, because the amine-sulfur trioxide complexes prepared from tertiary amines of higher base strengths normally react very slowly with the solvent and thus do not materially interfere with the desired sulfation reaction. Typical amines of this class include trimethylamine, triethylamine, tributylamine and N,N-dimethylbenzylamine. In general then, it can be said that the reaction is best carried out in a compatible solvent, i.e., a solvent which sufficiently solubilizes and does not cause undesirable side reactions with the particular base sulfur trioxide complex employed.

As explained, the addition of amounts of base to the reaction sufficient to render the $C_2$ hydroxyl of L-ascorbic acid or its salts more ionized than the $C_5$ and-/or $C_6$ hydroxyls thereof is essential in obtaining the improved results of this invention. The amount of base employed in a particular situation depends upon the amount of L-ascorbic acid or salt thereof originally used as well as the type of complex employed, and in general this amount can be defined broadly as above. If water is employed as a solvent in the reaction, the proper amount of base can be determined from the pH of the aqueous system. In such cases, a basic pH is required, preferably of from 8 to 13.5. In the most preferred form, a pH of from 10 to 10.5 has been found to be particularly advantageous.

The rationale for the use of these amounts of base in this context can be explained as follows: For purposes of illustration, it will be assumed that (a) the starting material is L-ascorbic acid, (b) water is employed as the solvent medium, and (c) sodium hydroxide is used as the free base to maintain a pH of about 10 to 10.5 during the reaction. It is to be understood however that the principles discussed are applicable to all of the species defined in this invention.

The amount of alkali needed to adjust the pH to the optimum level before addition of the amine-sulfur trioxide complex is determined by the amount of L-ascorbic acid used. When this pH level is attained, L-ascorbic acid consists of approximately a 50-50 mixture of the following two ionized forms:

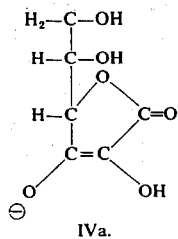
IVa.

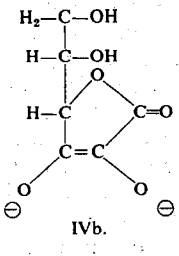
IVb.

To obtain this 50/50 mixture normally requires about 1.5 equivalents of NaOH, based upon the L-ascorbic acid. (It should be noted at this point that sulfation does not occur at the 3-position because of the instability of such species. This is true even though the 3-hydroxyl is completely ionized.)

At pH of about 10 to 10.5, the $C_5$ and $C_6$ hydroxyls of formulas IVa and IVb are much more weakly acidic hydroxyls than the $C_2$ hydroxyl, and their ionization is consequently very slight. The exact ionization constants of the $C_5$ and $C_6$ hydroxyls is not known, but they are believed to be very close to those of hydroxyls on sugars, e.g., approximately $10^{-12}$ to $10^{-13}$. Therefore, little ionization occurs at these positions, which is important in increasing the specificity of the desired sufation reaction.

An analysis of the formulas IVa. and IVb. will show the importance of ph, or, in the general case, the amount of base present during the sulfation reaction. First, it is believed that the speed of sulfation of the L-ascorbic acid depends upon the presence of molecules corresponding to formula IVb., where the $C_2$ hydroxyl is ionized. For this reason, the sulfation reaction increases with increasing pH and the yields of the desired derivatives improve. It is also known that L-ascorbate 2-sulfate is more stable at alkaline pH than L-ascorbate; therefore, if the 2-sulfate derivative forms more rapidly at higher pH, then less L-ascorbate will be lost prior to sulfation. In this manner, yields of L-ascorbate 2-sulfate improve by increasing the pH to moderate levels.

However, it has been found that several side reactions also commence with increasing pH, and if the ph level is too high, little of the desired 2-sulfated product is isolated. In some cases, a pH of above about 13 causes decreasing yield of the final product; therefore, it is felt that a pH of about 10 to 10.5 is optimum over a broad range of the possible reactions encompassed by this invention. The side reactions which occur are believed to include the following. First, the L-ascorbic acid is decomposed at very high pH levels, and a rapid loss of the base-sulfur trioxide complex by a reaction with the hydroxide ions instead of ascorbate ions also results. Additionally, it is also found that at extreme basicities the desired L-ascorbate 2-sulfate is sometimes destroyed even after it is formed.

In addition to the above, it is also believed that the presence of base is important for controlling the acidity of the reaction mixture during the sulfation step. This acidity is believed to result from several sources which can generate acid simultaneously with the desired sulfation. First, when L-ascorbic acid on a salt thereof is sulfated, the hydrogen of the 2-hydroxyl is replaced, thus causing H+ ions to be put into solution. The base portion of the base-sulfur trioxide complex normally takes up this acidity, if it is a sufficiently strong base. If not, extra free base will need to be added in order to compensate for this acidity. Additionally, the base-sulfur trioxide complex can react to produce acidic species according to the following general equation:

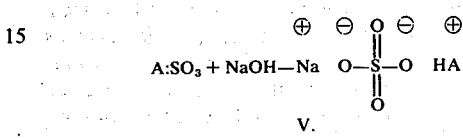
V.

It is believed that this reaction is primarily responsible for the consumption of base during the reaction.

Moreover, after the L-ascorbic acid has been sulfated, the free base present may serve to reverse the reaction in the following manner

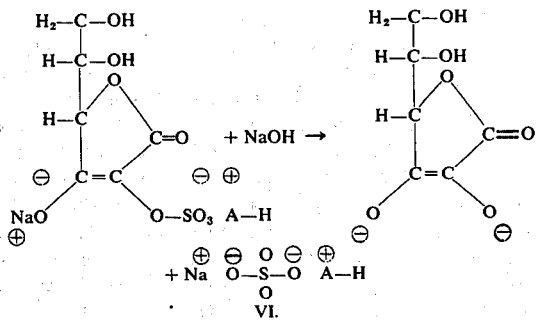
VI.

Lastly, the L-ascorbic acid itself in the presence of a base such as sodium hydroxide and oxygen can sometimes undergo oxidative destruction to produce further acidic species.

Therefore, the presence of added base serves to facilitate the sulfation reaction in two ways. It acts to ionize the $C_2$ hydroxyl of L-ascorbic acid to a level sufficient to permit the selective sulfation thereof; additionally, it serves to control the acidity of the reaction mixture during the sulfation step, as such acidity has been found to hinder the overall reaction.

The bases which can be added to the reaction include almost all bases, either organic or inorganic. The limitations upon the overall operability of the base selected would be its solubility, base strength and potential to react with the sulfur trioxide complex.

When bases such as pyridine with ionization constants of less than $10^{-8}$ are used, the required ionization of the $C_2$ hydroxyl is generally inefficient when compared to the action of stronger bases, thus requiring larger amounts of such bases. In addition, organic bases which contain reactive hydrogens sometimes compete with the L-ascorbic acid for the complex. For example, primary amines such as methylamine react with sulfur trioxide complexes to produce sulfamino derivatives of the amines. For this reason, the stronger inorganic metallic bases and the tertiary amines are preferred for use as the added free base.

When such strong bases such as sodium or barium hydroxide are used, they can be added in small incremental amounts to maintain the pH at the desired constant level during the sulfation reaction. When weak bases such as carbonates and bicarbonates, or strong bases having limited solubilities are employed, they may be added in large amounts in a single addition at the beginning of the reaction.

In another preferred embodiment of the present invention, L-ascorbic acid is reacted with trimethylamine sulfur trioxide complex, with water as the solvent medium. A pH of approximately 10 – 10.5 is maintained throughout the reaction by the addition of sodium hydroxide, and the reaction mixture is heated to a temperature of about 70°. Selection of the specific reagents and parameters is advantageous for several reasons. First, water, trimethylamine-sulfur trioxide, and sodium hydroxide are generally the least expensive reagents of the defined classes operable in the present invention, and are therefore desirable. Secondly, for the reasons outlined above, the pH and temperature levels given serve to accelerate the sulfation reaction without promoting the undesirable side reactions to an unacceptable degree. Likewise, the sulfated L-ascorbic acid produced under these conditions is easy to purify and the associated salts can be produced by conventional techniques.

After the completion of the initial sulfation reaction, it is usually necessary to separate and purify the sulfated products. This can be accomplished by any conventional method which serves to remove the base portion of the sulfurtrioxide complex and any inorganic sulfates formed during the reaction. The base portion of the complex, if left in the reaction mixture, will cause a number of undesirable products to form, and the inorganic sulfates should likewise be removed to achieve higher purities. These desired steps can be performed in a number of ways described below.

For example, when an apolar solvent has been employed, it is preferable to remove the base portion by evaporation, followed by adding aqueous alkali to a pH of about 11.0 to destroy any unreacted complex. The aqueous reaction mixture may then be treated in one of two ways. If the base portion of the complex is volatile, e.g., trimethylamine, it can be removed by further adjustment of the pH to about 12.5 followed by evaporation. It is preferable to adjust the pH with easily removable alkalis such as barium hydroxide, which can be removed by the formation of insoluable barium salts. Alternatively, the aqueous reaction mixture can be contacted with a cation exchange resin in the acid form to remove trimethylamine, metallic ions or the like. If such amines or metallic ions are not removed, then mixed salts containing these amine groups will be isolated in the final purification steps.

When it is desired to produce the associated salts of the sulfated product produced by the reaction defined above, the following steps have been found to be effective. First, the reaction mixture is contacted with a cation exchange resin in the acid form. Secondly, an acid acceptor containing a cation capable of bonding with any of inorganic sulfates present is added to the acidic solution off the resin. This serves the dual function of tying up any inorganic sulfates present (such as $SO_4^=$ ion formed by the hydrolysis of the complex), while the catonic portion of the acid acceptor forms a salt with the sulfated product of the initial reaction. Inorganic sulfate compounds which are formed can then be removed by well known fractional crystallization and filtration techniques.

In preferred forms, acid acceptors containing a metal taken from the group consisting of barium, calcium, magnesium, sodium, zinc, aluminum, ferrous, cobaltous, nickelous and potassium are employed. The most preferred forms thereof are the oxides, hydroxides and carbonates of barium, potassium, cobaltous and zinc. The advantages obtained through the use of these preferred acid acceptors are two-fold: first, the inorganic sulfates so produced can be removed by conventional techniques; secondly, the L-ascorbate 2-sulfate derivatives are readily crystallized as the salt and can be further purified with no difficulty. Such purification can consist of filtration and decolorization through charcoal, followed by concentration and recrystallization of the sulfated product. When so treated, the final product is generally 100% pure.

In order to produce the compounds having particular utility as vitamin C source additives, an acid acceptor is employed which contains a cation that is replaceable by other cations to form the desired salts. For example, when barium hydroxide is used as the acid acceptor, barium L-ascorbate 2-sulfate dihydrate is the final product of the original method. In such a case, the metal can optionally be replaced by a cationic replacement member selected from the group consisting of sodium, potassium, ammonium, pyridinium, calcium, magnesium, zinc, cobaltous, nickelous, aluminum and amino acids to produce the associated salts. Such replacement is most easily accomplished by adding an equimolar or greater amount of the sulfate salt of the defined cationic replacement members to an aqueous solution of the initial end product. This serves to produce L-ascorbate 2-sulfate salts represented by the formula

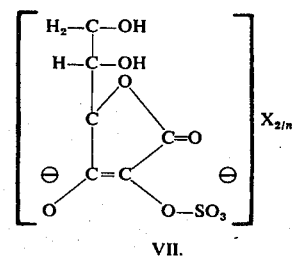

VII.

where X represents the cationic replacement members defined above and n represents the valence of the cation. Alternatively, these compounds can also be produced by contacting an aqueous solution of the original end product with a cation exchange resin which carries the replacement member as a cation thereon. The replacement member is thereby substituted for the original metal or other cation of the end product to produce compounds according to the above formula. In either case, the final additive compounds have been found to be of essentially 100% purity.

The following examples are meant to illustrate the present invention in its preferred embodiments, and are in no way to be construed as limitations thereon.

EXAMPLE I

To a mixture of water (5.0 ml) and L-ascorbic acid (1.15 × 10$^{-2}$ moles) was added 1 M aqueous sodium hydroxide until the pH of the mixture reached about 11.0. The solution was then warmed to about 70° C, and trimethylamine-sulfur trioxide (2.25 g, 1.62 × 10$^{-2}$ moles) was added. The pH of the solution was maintained at 10.8 – 11.0 by periodic addition of 1 M aqueous sodium hydroxide. After 0.5 hours, thin-layer chromatography showed complete disappearance of L-ascorbate, and analysis by UV spectroscopy indicated a quantitative conversion to L-ascorbate 2-sulfate. Water (20 ml) was added, and the solution was passed through a column of a cation exchange resin (100 ml) in the acid form. The effluent and the column washings were neutralized with barium hydroxide, the insoluble barium sulfate removed by filtration, and the filtrate concentrated to a small volume. Addition of methanol and cooling gave a crystalline solid (3.9 g) with m.p. 212°–219°. Recrystallization of the material gave pure barium L-ascorbate 2-sulfate dihydrate whose properties agreed in all respects with those of the compound prepared by previously stablished procedures. The isolated yield of this compound was approximately 80% by weight, and the purity thereof was essentially 100%. Quantitative conversion to L-ascorbate 2-sulfate was confirmed by a separate test wherein a 20% loss of L-ascorbate 2-sulfate occured when a known amount of this derivative was passed through a cation exchange resin and reisolated as the barium salt.

EXAMPLE II

To a mixture of water (5.0 ml) and potassium carbonate (2.24 × 10$^{-2}$ moles) was added a quantity of L-ascorbic acid (1.14 × 10$^{-2}$ moles). The solution was warmed to about 70° and trimethylamine-sulfur trioxide (2.40 g, 1.71 × 10$^{-2}$ moles) was added. After four hours stirring, thin-layer chromatography showed the reaction was complete. Water (20 ml) was added, and the solution was passed through a column of a cation exchange resin (100 ml) in the acid form. The effluent and the column washings were neutralized with barium hydroxide, the insoluble barium sulfate removed by filtration, and the filtrate concentrated to a small volume. Addition of methanol and cooling gave a crystalline solid (3.6 g) with m.p. 215°–218°. Recrystallization of the material gave pure barium L-ascorbate 2-sulfate dihydrate whose properties agreed in all respects with those of the compound prepared by previously established procedures. The yield of this compound was approximately 75% by weight, and the purity thereof was essentially 100%.

EXAMPLE III

A mixture of triemthylamine (1.34 g, 22.7 millimoles) and trimethylamine-sulfur trioxide complex (2.37g, 17.8 millimoles) in N,N-dimethylformamide (10 ml) was warmed to 70°. While stirring, L-ascorbic acid (2.0g, 11.4 millimoles) was added portion-wise over a period of five minutes. After 20 minutes at 70° thin-layer chromatography showed the reaction was complete. The solvent was removed by evaporation at reduced pressure, and water (50 ml) was added to the thick syrup followed by potassium carbonate (5g) to pH 10.5. The mixture was heated to 70° for 0.5 hour, cooled, and adjusted to a total volume of 100.0 ml. An aliquot of the solution was removed and diluted 2500 × with water. The absorbance of the diluted solution at pH 6.5 was 0.385, indicating an 80% conversion of L-ascorbate to L-ascorbate 2-sulfate. The reaction solution was passed through a cation exchange resin in the acid form, and the effluent from the column was neutralized with aqueous barium hydroxide. The insoluble barium sulfate was removed by filtration, and the filtrate was decolorized and concentrated to 30 ml. Addition of methanol (30 ml) and cooling gave 1.15 g (25%) of barium L-ascorbate 2-sulfate dihydrate with m.p. 200°–225°. Recrystallization gave the pure compound.

EXAMPLE IV

To a mixture of N,N-dimethylformamide (5 ml) and potassium L-ascorbate (2g, 9.35 × 10$^{-3}$ moles) at 70° was added trimethylamine-sulfur trioxide (1.9g, 14.0 × 10$^{-3}$ moles). (Alternatively, one can replace potassium L-ascorbate with sodium L-ascorbate (1.84g, 9.35 × 10$^{-3}$ moles).) The mixture gradually became homogeneous, and the reaction was complete in 30 minutes. The solvent was removed by evaporation at reduced pressure. The thick syrupy residue was dissolved in a small amount of water, and the mixture was passed through a strong cation exchange resin in the acid form. The acidic effluent off the column was neutralized by adding a barium base, such as barium hydroxide or barium carbonate. The total volume of the mixture was adjusted with water to solubilize the organic sulfate product, and the insoluble barium sulfate was removed by filtration. The aqueous filtrate was decolorized with charcoal and concentrated to a volume of 40 ml. Addition of methanol followed by cooling gave crystalline barium L-ascorbate 2-sulfate dihydrate (1.3g, 34%) with melting point 212°–220°.

EXAMPLE V

To a mixture of water (25.0) and L-ascorbic acid (2.0g, 11.5 millimoles) was added barium hydroxide octahydrate with stirring until the solution had pH 10.5. The mixture was warmed to 70°, and trimethylamine-sulfur trioxide (2.4g, 1.5 equivalent) was added. Solid barium hydroxide octahydrate was added intermittently to maintain the reaction pH at 10.5. A total of 5g of barium hydroxide octahydrate was used in the reaction to this point. After 30 minutes the reaction was complete as indicated by thin-layer chromatography. The mixture was cooled and a saturated aqueous solution of barium hydroxide (1–2 ml) was added to adjust the solution pH to 12.5. Nitrogen was passed through the mixture at 70° to expel trimethylamine. The solution was diluted with water (100 ml) and neutralized with aqueous sulfuric acid. Insoluble barium sulfate was removed by filtration, and the filtrate decolorized with charcoal and evaporated to a small volume (30 ml). Addition of methanol (30 ml) followed by cooling gave 3.94 g (80%) of barium L-ascorbate 2-sulfate dihydrate with m.p. 234°–40°.

The following example will serve to illustrate two preferred methods of isolating L-ascorbate 2-sulfates from the sulfation reaction.

EXAMPLE VI

Method 1. When trimethylamine or other volatile base is used both as the full base and as the base portion of the base-sulfur trioxide complex, or when trimethylamine is used as the free base and pyridine-sulfur trioxide is used as the complex, the following method has been found to be advantageous. By way of illustration, reaction mixture from a reaction of L-ascorbic acid in trimethylamine and water with trimethylamine-sulfur trioxide complex can be adjusted to pH 12.5 by addition of aqueous barium hydroxide. Nitrogen is passed through the mixture at 70° to remove trimethylamine.

The mixture is thereafter cooled and neutralized with aqueous sulfuric acid, and barium sulfate is removed by filtration. The final step involves concentration of the filtrate, addition of methanol and crystallization of barium L-ascorbate 2-sulfate dihydrate.

Method 2. This method is applicable to the use of all bases and sulfur trioxide complexes. The reaction mixture from reaction of L-ascorbic acid in aqueous alkaline medium with a base-sulfur trioxide complex is contacted with a strong cation exchange resin in the acid form, and the acidic solution off the resin is neutralized with aqueous barium hydroxide. Insoluble barium sulfate is thereafter removed by filtration and the filtrate is concentrated and diluted with methanol to crystallize barium L-ascorbate 2-sulfate dihydrate.

If a dipolar aprotic solvent such as N,N-dimethylformamide is used instead of water in the sulfation of L-ascorbic acid then several other steps are followed prior to using Method 1 or Method 2 above. These steps include evaporating the reaction mixture to a thick syrup to remove the solvent. If the base and amine portion of the complex are volatile (e.g., trimethylamine and pyridine-sulfur trioxide complex), then Method 1 above can be followed. In that case water is added, followed by aqueous barium hydroxide to adjust the pH to about 12.5. Subsequently the mixture is evaporated, cooled, neutralized with acid and the barium sulfate is removed and the filtrate treated as described to yield the desired product.

In alternate procedures, the thick syrup can be dissolved in water and contacted with a cation exchange resin in the acid form. The acidic solution off the resin is then neutralized with barium hydroxide and barium sulfate removed by filtration. The filtrate is thereafter treated as in Method 2 to give barium L-ascorbate 2-sulfate dihydrate.

The following examples serve to illustrate the ways of replacing the barium on the salts produced by the methods of Examples I – V with a desired cationic replacement member, to produce the final salts which serve as vitamin C sources in food systems.

EXAMPLE VII

Barium L-ascorbate 2-sulfate dihydrate (2.0g) was dissolved in water (100 ml) and one equivalent of potassium sulfate (0.81 g) was added. The mixture was stirred 30 minutes, and insoluble barium sulfate removed by filtration. Evaporation of the water gave 1.53 g (97.5%) of crystalline dispotassium L-ascorbate 2-sulfate, m.p. 87°–89.5°, $[\alpha]_D^{25} + 55°$ (c 1.0, water). U.V. data: $\lambda$ max = 255 nm ($\epsilon$ = 21,700) at pH 7.2, and $\lambda$ max = 232 nm ($\epsilon$ = 14,100) at pH 2.1.

EXAMPLE VIII

Barium L-ascorbate 2-sulfate dihydrate (3.0g) was dissolved in water (100 ml) and the aqueous solution was passed through a cation exchange resin (1.75 milliequivalents/ml) in the potassium form. The column was washed with one-bed volume of water, the effluents combined and then concentrated to dryness. The residue (1.8 g, 77%) was pure dispotassium L-ascorbate 2-sulfate which was identical in all respects to that prepared in Example VII.

EXAMPLE IX

Barium L-ascorbate 2-sulfate dihydrate (1.0g) was dissolved in water (30 ml), and the solution was passed through a strong cation exchange resin in the L-alaninium form. The column effluent and washings were combined and concentrated to a syrup. Crystallization was effected from a mixture of acetone and ethyl ether. The crystalline solid (6.4g, 80%) had melting point of 155°–60°. The salt had the correct ratio of methyl to C-4 protons for a mono-L-alaninium salt.

EXAMPLE X

In this method the effluent off the cation exchange resin (acid form) in the original sulfation reaction is neutralized with a base of the desired cation to give a mixture of an inorganic salt and the desired salt of L-ascorbate 2-sulfate.

The effluent from the column in the above reaction of 10 g of 5,6-O-isopropylidene-L-ascorbic acid was adjusted to pH 7.0 with a potassium base, such as potassium hydroxide or potassium carbonate. The solution was concentrated to dryness. The solid material (19 g) was shown by ultraviolet spectroscopy to contain 61% dipotassium L-ascorbate 2-sulfate mixed with potassium sulfate.

The following examples illustrate other cationic replacement members which can be used in the methods outlined in Example VII, VIII and X, it being noted that the latter method gives mixtures of inorganic and organic sulfates. In each case, they can be produced by either of the three methods described. What follows is experimental data for each of the final compounds showing parameters which demonstrate their purity and structure.

EXAMPLE XI

Pyridinium L-ascorbate 2-sulfate is a dimorphic crystalline solid with m.p. 119°–120.5° or 133°–4°, $[\alpha]_D^{25} + 40°$ (c 1.0, water). The nuclear magnetic resonance spectrum of the compound gave the correct proportion of aromatic to ascorbic acid protons for the monopyridinium salt.

Calc. for $C_{11}H_{12}NO_9S$: C, 39.52; H, 362; S, 9.59. Found: C, 39.69; H, 3.72; S, 9.57.

EXAMPLE XII

Sodium L-ascorbate 2-sulfate was produced, and under a light microscope it appears to be a mixture of crystalline and amorphous solids with m.p. 150°–250°, $[\alpha]_D^{25} + 50°$ (c 1.0, water).

Elemental analysis: Calc. for $C_6H_6Na_2O_9S$: C, 24.01; H, 2.02. Found: C, 23.35; H, 2.09.

EXAMPLE XIII

The zinc L-ascorbate 2-sulfate dihydrate produced according to the invention is a crystalline solid, m.p. 185°–188°, $[\alpha]_D^{25} + 50°$ (c 1.0, water). Elemental analysis indicates the compound has the following empirical formula: $C_6H_6ZnO_9S \cdot 2H_2O$, which gives the following calculated percentages:

C, 20.27; H, 2.84. Found: C, 20.26; H, 3.15.

EXAMPLE XIV

The cobaltous L-ascorbate 2-sulfate dihydrate produced is a crystalline solid, m.p. 196°–198°, $[\alpha]_D^{25} + 50°$ (c 1.0 water).

Elemental analysis: Cal. for $C_6H_6CoO_9S \cdot 2H_2O$: C, 20.62; H, 2.88. Found: C, 20.31; H, 2.18.

Other salt derivatives of L-ascorbate 2-sulfate with their replacement member and respective melting points are as follows: ferrous, 175°–185°; diammonium, 190°; and aluminum, 196°–8°. All these salts have $[\alpha]_D^{25} + 50°$ (c 1.0, water).

EXAMPLE XV

The magnesium L-ascorbate 2-sulfate is a hygroscopic solid having m.p. 134°–6° and $[\alpha]_D^{25} + 50°$ (c 1.0, water). The solid appears amorphous when viewed under the light microscope.

Cal. for $C_6H_6MgO_9S$: C, 25.88; H, 2.17; S, 11.5. Found: C, 25.62; H, 2.24; S, 10.86.

EXAMPLE XVI

The calcium L-ascorbate 2-sulfate is an hygroscopic, amorphous solid with melting point 208°–210° and $[\alpha]_D^{25} + 50°$ (c 1.0, water).

Cal. for $C_6H_6CaO_9S$: C, 24.49; H, 2.06; S, 10.90. Found: C, 24.33; H, 2.02; S, 10.86.

What is claimed is:

1. A method of producing L-ascorbate 2-sulfate compounds which comprises the steps of:

reacting in a non-interfering aqueous solvent which does not substantially hinder the desired sulfation reaction a compound selected from the group consisting of L-ascorbic acid and salts thereof of the formula

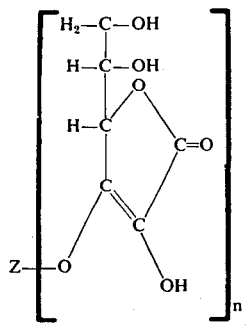

where Z is selected from the group consisting of hydrogen, the alkali metals, the alkaline earth metals and tertiary amines, and n represents the valence of Z, with a sulfur trioxide complex of the formula

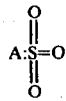

where A is selected from the group consisting of trimethylamine, triethylamine, tributylamine and N,N-dimethylbenzylamine; and adding sufficient base selected from the group consisting of the inorganic metallic bases and tertiary amines to the reaction mixture to maintain the latter at a basic pH level for increasing the selectivity of sulfation at the 2-hydroxyl of said first-mentioned reactant.

2. The method as set forth in claim 1 wherein said aqueous solvent is selected from the group consisting of water and mixtures of alcohol and water.

3. The method as set forth in claim 1 wherein said base is selected from the group consisting of sodium hydroxide, barium hydroxide, potassium carbonate and trimethylamine.

4. The method as set forth in claim 1 wherein sufficient base is added to said reaction mixture to maintain the pH thereof at a level of from about 10.0 to 10.5.

5. The method as set forth in claim 1 wherein said reaction is carried out at a temperature within the range of from about 40° to 90° C.

6. The method of claim 1 wherein is included the steps of:

removing the base portion of said sulfur trioxide complex from the reaction mixture after said sulfation reaction is complete; and removing from said reaction mixture any inorganic sulfates produced during said sulfation reaction.

7. The method of claim 6 wherein is included the step of removing said base portion of said complex by adding water to said reaction mixture and contacting the aqueous reaction mixture with a cation exchange resin in acid form.

8. The method of claim 6 wherein is included the steps of:

employing a sulfur trioxide complex, the base portion thereof being easily volatizible, in the initial sulfation reaction;

adjusting the pH of said reaction mixture after said sulfation reaction to a level of about 12.5; and expelling said volatile base portion of said complex from said reaction mixture by passage of an inert gas through said reaction mixture.

9. The method of claim 6 wherein is included the steps of:

removing said inorganic sulfates by adding to said reaction mixture an acid acceptor selected from the group consisting of the oxides, hydroxides, and carbonates of barium, potassium, cobaltous and zinc to thereby form a salt with the sulfates product.

* * * * *